United States Patent
Wang et al.

(10) Patent No.: US 10,242,441 B2
(45) Date of Patent: Mar. 26, 2019

(54) IDENTIFYING LIVING SKIN TISSUE IN A VIDEO SEQUENCE USING COLOR AND SPATIAL SIMILARITIES

(71) Applicant: KONINKLIJKE PHILIPS N.V., Eindhoven (NL)

(72) Inventors: Wenjin Wang, Eindhoven (NL); Gerard De Haan, Helmond (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1 day.

(21) Appl. No.: 15/157,452

(22) Filed: May 18, 2016

(65) Prior Publication Data

US 2016/0343130 A1    Nov. 24, 2016

(30) Foreign Application Priority Data

May 21, 2015 (EP) .................... 15168566

(51) Int. Cl.
*G06K 9/00* (2006.01)
*G06K 9/62* (2006.01)
(Continued)

(52) U.S. Cl.
CPC .......... *G06T 7/0012* (2013.01); *A61B 5/0077* (2013.01); *A61B 5/02416* (2013.01); *A61B 5/7485* (2013.01); *G06K 9/00114* (2013.01); *G06K 9/00228* (2013.01); *G06K 9/00234* (2013.01); *G06K 9/00268* (2013.01); *G06K 9/00496* (2013.01); *G06K 9/622* (2013.01); *G06K 9/624* (2013.01); *G06K 9/6215* (2013.01);
(Continued)

(58) Field of Classification Search
None
See application file for complete search history.

(56) References Cited

U.S. PATENT DOCUMENTS

| 8,311,277 B2 * | 11/2012 | Peleg ............... G06F 17/3079 382/103 |
| 2010/0092037 A1 * | 4/2010 | Peleg ............... G06F 17/3079 382/103 |

(Continued)

OTHER PUBLICATIONS

Galasso, et al., "Video Segmentation with Superpixels", Computer Vision Accv 2012, Springer Berlin Heidelberg.

(Continued)

*Primary Examiner* — Tahmina N Ansari

(57) ABSTRACT

According to an aspect, there is provided an apparatus for identifying living skin tissue in a video sequence, the apparatus comprising a processing unit configured to receive a video sequence, the video sequence comprising a plurality of image frames; divide each of the image frames into a plurality of frame segments, wherein each frame segment is a group of neighboring pixels in the image frame; form a plurality of video sub-sequences, each video sub-sequence comprising a frame segment from two or more of the plurality of image frames; analyze the plurality of video sub-sequences to determine a pulse signal for each video sub-sequence; determine a similarity matrix based on pairwise similarities for each determined pulse signal with each of the other determined pulse signals; and identify areas of living skin tissue in the video sequence from the similarity matrix.

18 Claims, 11 Drawing Sheets

(51) Int. Cl.
    G06T 7/00      (2017.01)
    A61B 5/024     (2006.01)
    A61B 5/00      (2006.01)
(52) U.S. Cl.
    CPC .... *G06K 9/6232* (2013.01); *A61B 2562/0233* (2013.01); *A61B 2576/00* (2013.01); *G06K 9/00906* (2013.01); *G06T 2207/10016* (2013.01); *G06T 2207/20021* (2013.01); *G06T 2207/30088* (2013.01)

(56) References Cited

U.S. PATENT DOCUMENTS

| | | | | |
|---|---|---|---|---|
| 2012/0195473 | A1* | 8/2012 | De Haan | G06T 7/20 382/107 |
| 2013/0345569 | A1* | 12/2013 | Mestha | A61B 5/0044 600/473 |
| 2015/0250391 | A1* | 9/2015 | Kyal | A61B 5/0077 382/128 |
| 2016/0338604 | A1* | 11/2016 | Wang | A61B 5/02416 |
| 2016/0343130 | A1* | 11/2016 | Wang | G06T 7/0012 |
| 2016/0343135 | A1* | 11/2016 | De Haan | A61B 5/0077 |

OTHER PUBLICATIONS

Gibert Guillaume et al: "Face detection method based on photoplethysmography", 2013 10th IEEE International Conference on Advanced Video and Signal Based Surveillance, IEEE, Aug. 27, 2013 (Aug. 27, 2013), pp. 449-453.

Litong Feng et al: "Dynamic ROI based on K-means for remote photoplethysmography", 2015 IEEE International Conference on Acoustics, Speech and Signal Processing (ICASSP), Apr. 1, 2015 (Apr. 1, 2015), pp. 1310-1314.

Ron Van Luijtelaar et al: "Automatic Roi Detection for Camera-Based Pulse-Rate Measurement" In: "Lecture Notes in Computer Science", Nov. 2, 2014.

He Liu et al: "A New Approach for Face Detection Based on Photoplethysmographic Imaging" In: "Grid and cooperative computing—GCC 2004 : third international conference, Wuhan, China, Oct. 21-24, 20041N: Lecture notes in computer science , ISSN 0302-9743 ; vol. 3251", May 6, 2015.

Reso Matthias et al: "Temporally Consistent Superpixels", 2013 IEEE International Conference on Computer Vision, IEEE, Dec. 1, 2013, pp. 385-392.

Sylvain Paris et al: "A gentle introduction to bilateral filtering and its applications", Computer Graphics Proceedings, Proceedings of SIGGRAPH AnnualInternational Conference on Computer Graphics and InteractiveTechniques, Aug. 5, 2007, pp. 1-45.

Rubinstein, "Analysis and Visualization of Temporal Variations in Video", Feb. 2014, Massachusetts Institute of Technology.

Poh, et al., "Non-contact, automated cardiac pulse measurements using video imaging and blind source separation", May 10, 2010 / vol. 18, No. 10 / Optics Express.

Li, et al., "Remote Heart Rate Measurement from Face Videos Under Realistic Situations", 2014 IEEE Conference on Computer Vision and Pattern Recognition.

Balakrishnan, et al., "Detecting Pulse from Head Motions in Video", Computer Vision and Pattern Recognition (CVPR), 2013 IEEE Conference on Jun. 23-28, 2013.

Achanta, et al,. "SLIC Superpixels Compared to State-of-the-art Superpixel Methods", IEEE Transactions on Pattern Analysis & Machine Intelligence 2012 vol. 34 Issue No. 11, Nov. 2012, pp. 2274-2282.

de Haan, et al., "Robust pulse rate from chrominance-based rPPG", TBME, 60(1):2878-2886, 2013.

de Haan, et al., "Improved motion robustness of remote-PPG by using the blood volume pulse signature", Physiol. Meas. 35 1913, 2014.

Viola, et al., "Rapid object detection using a boosted cascade of simple features", CVPR, 2001.

Dalal, et al., "Histograms of oriented gradients for human detection", CVPR, 2005, 1.

Zhang, et al., "Sparse PCA: Convex relaxations, algorithms and applications", International Series in Operations Research & Management Science vol. 166:915-940, 2012.

Argyriou, et al., "Hybrid conditional gradient-smoothing algorithms with applications to sparse and low rank regularization", arXiv preprint: 1404.3591, 2014.

* cited by examiner

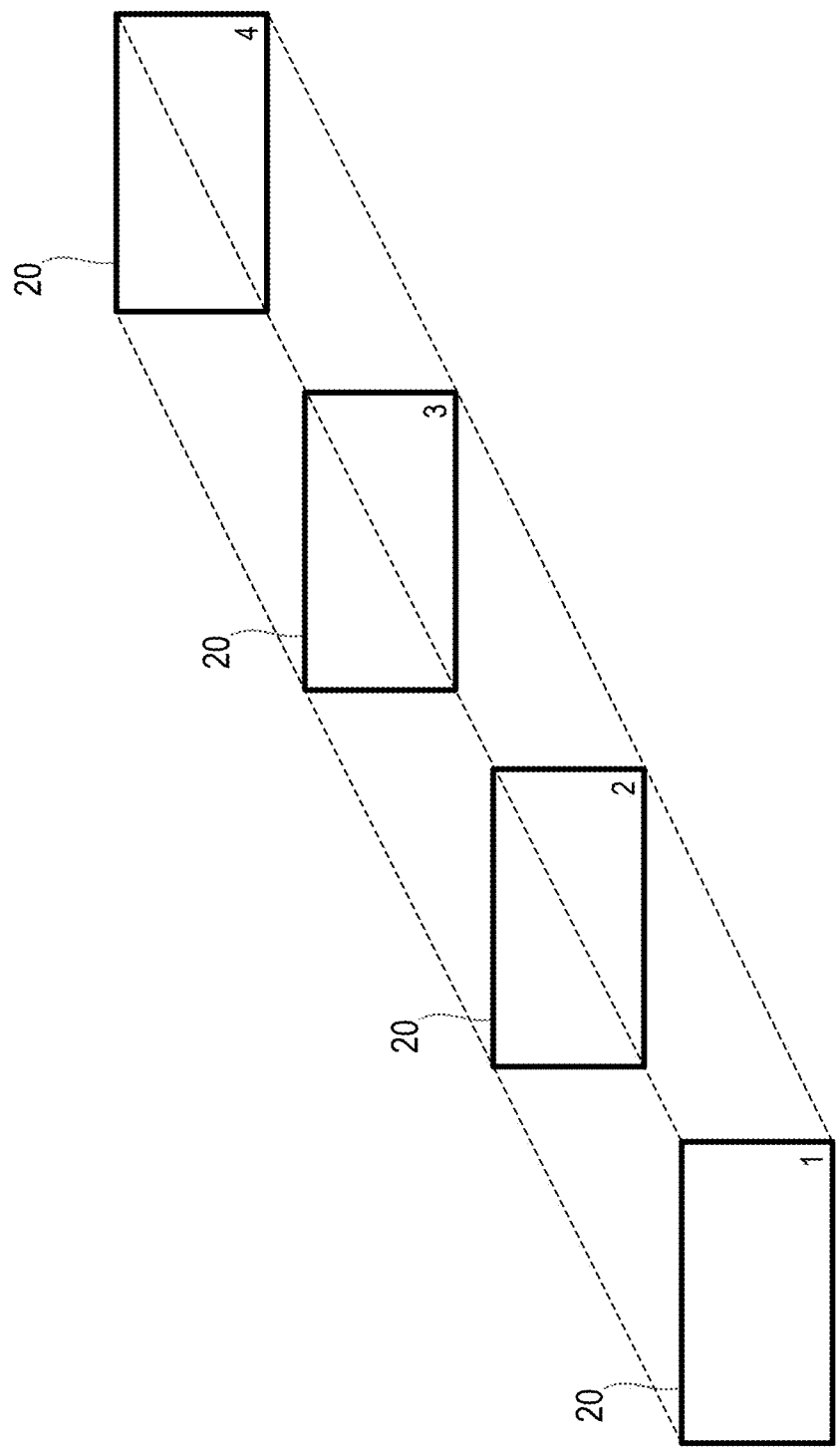

IDENTIFYING LIVING SKIN TISSUE IN A VIDEO SEQUENCE USING COLOR AND SPATIAL SIMILARITIES

CROSS REFERENCE TO RELATED APPLICATIONS

This application claims the benefit of European Patent Application Number 15168566 filed May 21, 2015. This application is hereby incorporated by reference herein.

TECHNICAL FIELD OF THE INVENTION

The invention relates to an apparatus and method for identifying living skin tissue in a video sequence.

BACKGROUND OF THE INVENTION

Recently, techniques for performing remote photoplethysmography (remote PPG or rPPG) have been developed. These techniques enable a PPG signal to be obtained from a video sequence of image frames captured using an imaging unit (e.g. a camera). It is desirable for a video sequence to be processed and rPPG signals extracted automatically so that subjects can be automatically monitored. However, this requires areas of living skin tissue to be automatically identified in the video sequence.

The task of detecting subjects in a video, as one of the fundamental topics in computer vision, has been extensively studied in the past decades. Given a video sequence containing subjects, the goal is to locate the regions corresponding to the body parts of a subject. Most existing work exploits human appearance features to discriminate between subject and background in a supervised training mechanism. However, a common problem with these methods is that their trained features are not unique to human beings, any feature that is similar to human appearance can be misclassified. Moreover, supervised methods are usually restricted to prior-known samples and tend to fail when unpredictable samples occur, e.g. a face detector trained with frontal faces cannot locate faces viewed from the side, while a skin classifier trained with bright skin subjects fails with dark skin subjects.

Based on the development of rPPG techniques, it has been observed that as compared to physical appearance features, the invisible physiological features (e.g. pulse) can better differentiate humans from non-humans in a video sequence. In the natural environment, only the skin tissue of an alive subject exhibits pulsatility, so any object that does not show a pulse-signal can be safely classified into the non-human category. This can prevent the false detection of objects with an appearance similar to humans, as shown, for example, in FIG. 1.

FIG. 1 provides two examples of how a living tissue detection technique should successfully operate. In the left hand image, a human face and an artificial face are present face on to the camera, and only the human face should be identified (despite the artificial face having similar physical appearance features to the human face), as indicated by the dashed box and outline of the area corresponding to living skin tissue. In the right hand image, a human face and an artificial face are present side on to the camera, and only the human face should be identified.

In the paper "Face detection method based on photoplethysmography" by G. Gibert and D. D'Alessandro, and F. Lance, 10th IEEE International Conference on Advanced Video and Signal Based Surveillance (AVSS), pp. 449-453, (2013) a hard threshold is set to select segmented local regions (e.g. grids, triangles or voxels) with higher frequency spectrum energy as skin-regions. In the paper "Automatic ROI detection for rPPG measurements" by R. van Luijtelaar, W. Wang, S. Stuijk, and G. de Haan, ACCV 2014, Singapore pre-defined clustering parameters are used to cluster regions sharing similarities as skin regions.

However, these methods are not parameter free and are not robust to realistic challenges from practical use-cases, i.e. a hard threshold tuned on adults is not applicable to neonates; and a pre-defined cluster number or density is not flexible to multi-subject detection.

Therefore it is an object to provide an improved method and apparatus for identifying living skin tissue in a video sequence.

SUMMARY OF THE INVENTION

According to a first aspect, there is provided a method for identifying living skin tissue in a video sequence, the method comprising obtaining a video sequence, the video sequence comprising a plurality of image frames; dividing each of the image frames into a plurality of frame segments, wherein each frame segment is a group of neighboring pixels in the image frame; forming a plurality of video sub-sequences, each video sub-sequence comprising a frame segment from two or more of the plurality of image frames; analyzing the plurality of video sub-sequences to determine a pulse signal for each video sub-sequence; determining a similarity matrix based on pairwise similarities for each determined pulse signal with each of the other determined pulse signals; and identifying areas of living skin tissue in the video sequence from the similarity matrix.

In some embodiments the step of determining a similarity matrix can comprise determining the pairwise similarities; and forming the similarity matrix by combining the determined pairwise similarities.

In some embodiments the step of determining the pairwise similarities can comprise determining, for each pulse signal, a measure of pairwise similarity between the pulse signal and each of the other pulse signals.

In alternative embodiments, the step of determining the pairwise similarities can comprise determining two or more measures of pairwise similarity for each pulse signal with each of the other pulse signals; and combining the two or more measures of pairwise similarity for each pulse signal to form distance metrics representing the pairwise similarity for each pulse signal with each of the other pulse signals; wherein the similarity matrix is determined based on the distance metrics.

In some embodiments, the pairwise similarity for a pulse signal and one of the other pulse signals can comprise a measure of the correlation between the frequency spectra of the two pulse signals. In alternative or further embodiments, the pairwise similarity for a pulse signal and one of the other pulse signals can comprise a measure of the normalized cross correlation between the frequency spectra of the two pulse signals. In alternative or further embodiments, the pairwise similarity for a pulse signal and one of the other pulse signals can comprise a measure of the regularity of correlation between the frequency spectra of the two pulse signals. In alternative or further embodiments, the pairwise similarity for a pulse signal and one of the other pulse signals can comprise the result of an inner product of the two pulse signals.

In some embodiments, the pairwise similarities can include frequency-based pairwise similarities.

In some embodiments, the step of identifying areas of living skin tissue in the sequence of images from the similarity matrix can comprise performing matrix decomposition on the similarity matrix.

In some embodiments, performing matrix decomposition can comprise using one or more of singular value decomposition, SVD, QR decomposition, sparse SVD, incremental SVD, principal component analysis, PCA, and independent component analysis, ICA.

Each frame segment is typically a group of neighboring pixels in the image frame. In some embodiments, each frame segment has the same shape. In alternative embodiments, the step of dividing each of the image frames into a plurality of frame segments comprises grouping pixels into frame segments based on color and spatial similarities of the pixels.

In some embodiments, the step of forming a plurality of video sub-sequences can comprise forming each video sub-sequence from frame segments in corresponding spatial positions in the plurality of image frames. In alternative embodiments, the step of forming a plurality of video sub-sequences can comprise, for each video sub-sequence, selecting frame segments from each of the plurality of image frames such that a chromatic energy and/or spatial-distance energy between the frame segments in the video sub-sequence is minimized.

In some embodiments, the step of analyzing the video sub-sequences to determine a pulse signal can comprise averaging pixel values for each pixel in a frame segment; and forming the pulse signal for a video sub-sequence from the averaged pixel values for each frame segment in the video sub-sequence.

In some embodiments, the step of averaging pixel values comprises weighting the pixel values of pixels in a frame segment, wherein the pixel values are weighted based on spatial position of the pixel in the frame segment and/or a difference in color with a pixel or group of pixels at or near the center of the frame segment; and averaging the weighted pixel values of pixels in a frame segment.

In some embodiments, the method further comprises the step of determining one or more physiological characteristics from one or more pulse signals associated with the identified areas of living skin tissue in the video sequence.

According to a second aspect there is provided a computer program product comprising a computer readable medium having computer readable code embodied therein, the computer readable code being configured such that, on execution by a suitable computer or processor, the computer or processor is caused to perform any of the methods set out above.

According to a third aspect, there is provided an apparatus for identifying living skin tissue in a video sequence, the apparatus comprising a processing unit configured to receive a video sequence, the video sequence comprising a plurality of image frames; divide each of the image frames into a plurality of frame segments, wherein each frame segment is a group of neighboring pixels in the image frame; form a plurality of video sub-sequences, each video sub-sequence comprising a frame segment from two or more of the plurality of image frames; analyze the plurality of video sub-sequences to determine a pulse signal for each video sub-sequence; determine a similarity matrix based on pairwise similarities for each determined pulse signal with each of the other determined pulse signals; and identify areas of living skin tissue in the video sequence from the similarity matrix.

In some embodiments the processing unit is configured to determine a similarity matrix by determining the pairwise similarities and forming the similarity matrix by combining the determined pairwise similarities.

In some embodiments the processing unit is configured to determine the pairwise similarities by determining, for each pulse signal, a measure of pairwise similarity between the pulse signal and each of the other pulse signals.

In alternative embodiments, the processing unit is configured to determine the pairwise similarities by determining two or more measures of pairwise similarity for each pulse signal with each of the other pulse signals and combining the two or more measures of pairwise similarity for each pulse signal to form distance metrics representing the pairwise similarity for each pulse signal with each of the other pulse signals; wherein the similarity matrix is determined based on the distance metrics.

In some embodiments, the pairwise similarity for a pulse signal and one of the other pulse signals can comprise a measure of the correlation between the frequency spectra of the two pulse signals. In alternative or further embodiments, the pairwise similarity for a pulse signal and one of the other pulse signals can comprise a measure of the normalized cross correlation between the frequency spectra of the two pulse signals. In alternative or further embodiments, the pairwise similarity for a pulse signal and one of the other pulse signals can comprise a measure of the regularity of correlation between the frequency spectra of the two pulse signals. In alternative or further embodiments, the pairwise similarity for a pulse signal and one of the other pulse signals can comprise the result of an inner product of the two pulse signals.

In some embodiments, the pairwise similarities can include frequency-based pairwise similarities.

In some embodiments, the processing unit is configured to identify areas of living skin tissue in the sequence of images from the similarity matrix by performing matrix decomposition on the similarity matrix.

In some embodiments, the processing unit is configured to perform matrix decomposition using one or more of singular value decomposition, SVD, QR decomposition, sparse SVD, incremental SVD, principal component analysis, PCA, and independent component analysis, ICA.

Each frame segment is typically a group of neighboring pixels in the image frame. In some embodiments, each frame segment has the same shape. In alternative embodiments, the processing unit is configured to divide each of the image frames into a plurality of frame segments by grouping pixels into frame segments based on color and spatial similarities of the pixels.

In some embodiments, the processing unit is configured to form a plurality of video sub-sequences by forming each video sub-sequence from frame segments in corresponding spatial positions in the plurality of image frames. In alternative embodiments, the processing unit is configured to form a plurality of video sub-sequences by, for each video sub-sequence, selecting frame segments from each of the plurality of image frames such that a chromatic energy and/or spatial-distance energy between the frame segments in the video sub-sequence is minimized.

In some embodiments, the processing unit is configured to analyze the video sub-sequences to determine a pulse signal by averaging pixel values for each pixel in a frame segment; and forming the pulse signal for a video sub-sequence from the averaged pixel values for each frame segment in the video sub-sequence.

In some embodiments, the processing unit is configured to average pixel values by weighting the pixel values of pixels in a frame segment, wherein the pixel values are weighted based on spatial position of the pixel in the frame segment and/or a difference in color with a pixel or group of pixels at or near the center of the frame segment; and averaging the weighted pixel values of pixels in a frame segment.

In some embodiments, the processing unit is further configured to determine one or more physiological characteristics from one or more pulse signals associated with the identified areas of living skin tissue in the video sequence.

In some embodiments, the apparatus further comprises an imaging unit for capturing the video sequence.

BRIEF DESCRIPTION OF THE DRAWINGS

For a better understanding of the invention, and to show more clearly how it may be carried into effect, reference will now be made, by way of example only, to the accompanying drawings, in which:

FIGS. 4(a)-(d) illustrate how pulse signals for a plurality of video sub-sequences can be obtained from a video sequence;

FIG. 4(a) illustrates how a video sequence is made up of a series of image frames;

FIG. 4(b) illustrates how each of the image frames is divided into a plurality of frame segments;

FIG. 4(c) illustrates how two video sub-sequences are formed using frame segments in the same spatial position within the image frames;

FIG. 4(d) illustrates exemplary pulse signals for the two video subsequences so formed;

DETAILED DESCRIPTION OF THE PREFERRED EMBODIMENTS

Figure 2:
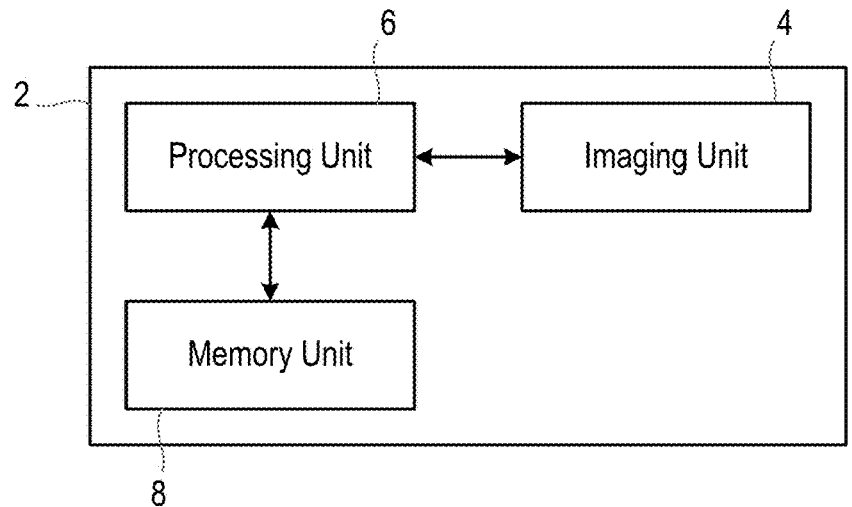
FIG. 2 is a block diagram of an apparatus according to an embodiment of the invention.

An apparatus 2 that can be used to identify living skin tissue according to an embodiment of the invention is shown in FIG. 2. The apparatus 2 comprises an imaging unit 4 that captures a video sequence over a period of time. The imaging unit 4 can be or comprise a camera, for example an RGB camera, that can be used for rPPG measurements. The imaging unit 4 provides a video sequence comprising a plurality of image frames to a processing unit 6.

The processing unit 6 controls the operation of the apparatus 2 and can comprise one or more processors, multi-core processors or processing modules for implementing the living skin tissue identification techniques described herein. In some embodiments, the processing unit 6 can be implemented as a plurality of processing modules, with each module being configured to perform a particular part or step of the living skin tissue identification techniques described herein.

The apparatus 2 further comprises a memory unit 8 for storing computer readable program code that can be executed by the processing unit 6 to perform the method according to the invention. The memory unit 8 can also be used to store or buffer the video sequence from the imaging unit 4 before, during and after processing by the processing unit 6 and any intermediate products of the processing.

It will be appreciated that in some embodiments the apparatus 2 can comprise a general-purpose computer (e.g. a desktop PC) with an integrated or separate imaging unit 4, or a portable computing device (e.g. a laptop, tablet or smart phone) that has an integrated or separate imaging unit 4. In some embodiments, the apparatus 2 can be dedicated to the purpose of identifying living skin tissue in a video sequence, and/or for measuring physiological characteristics of a subject from rPPG signals extracted from areas of a video sequence identified as corresponding to living skin tissue.

In practical implementations, the apparatus 2 may comprise other or further components to those shown in FIG. 2 and described above, such as a user interface that allows a subject to activate and/or operate the apparatus 2, and a power supply, such as a battery or connection to a mains power supply, for powering the apparatus 2. The user interface may comprise one or more components that allow a subject to interact and control the apparatus 2. As an example, the one or more user interface components could comprise a switch, a button or other control means for activating and deactivating the apparatus 2 and/or living skin tissue identification process. The user interface components can also or alternatively comprise a display, or other visual indicator (such as a light) for providing information to the subject about the operation of the apparatus 2. Likewise, the user interface components can comprise an audio source for providing audible feedback to the subject about the operation of the apparatus 2.

Figure 3:
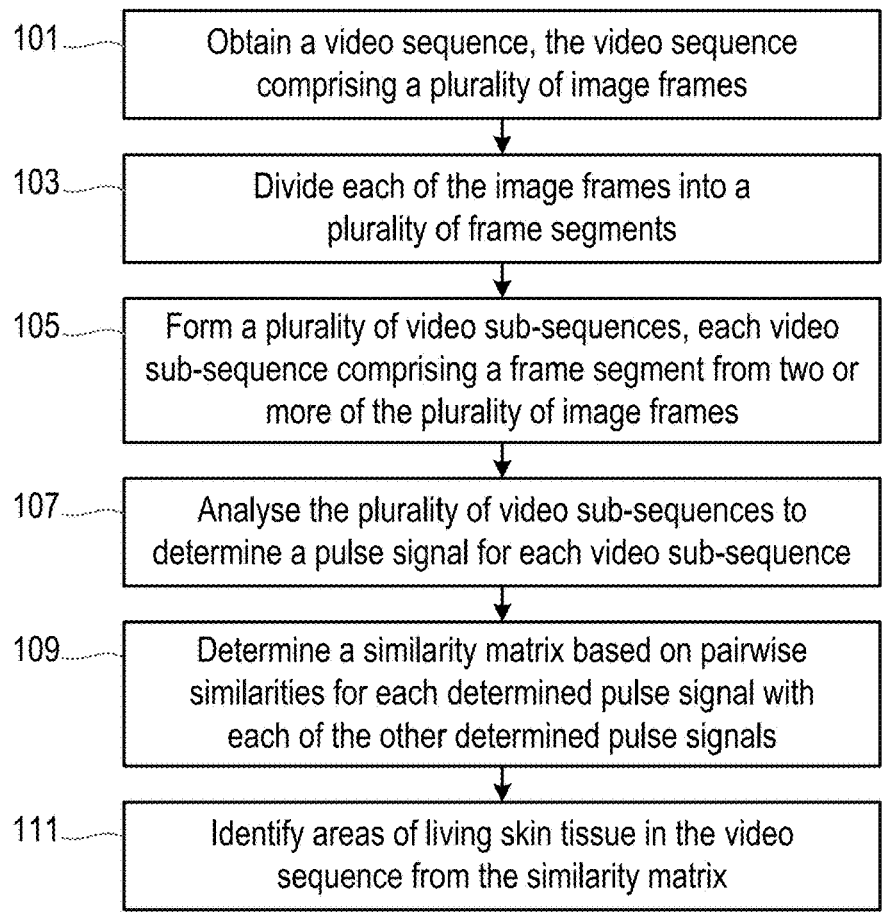
FIG. 3 is a flow chart illustrating a method according to an embodiment of the invention.

The flow chart in FIG. 3 illustrates a method of identifying living skin tissue in a video sequence according to an embodiment.

In step 101, an imaging unit 4 obtains a video sequence. The video sequence is made up of a series of image frames. A series of image frames 20 is shown in FIG. 4(a).

Figure 4B:
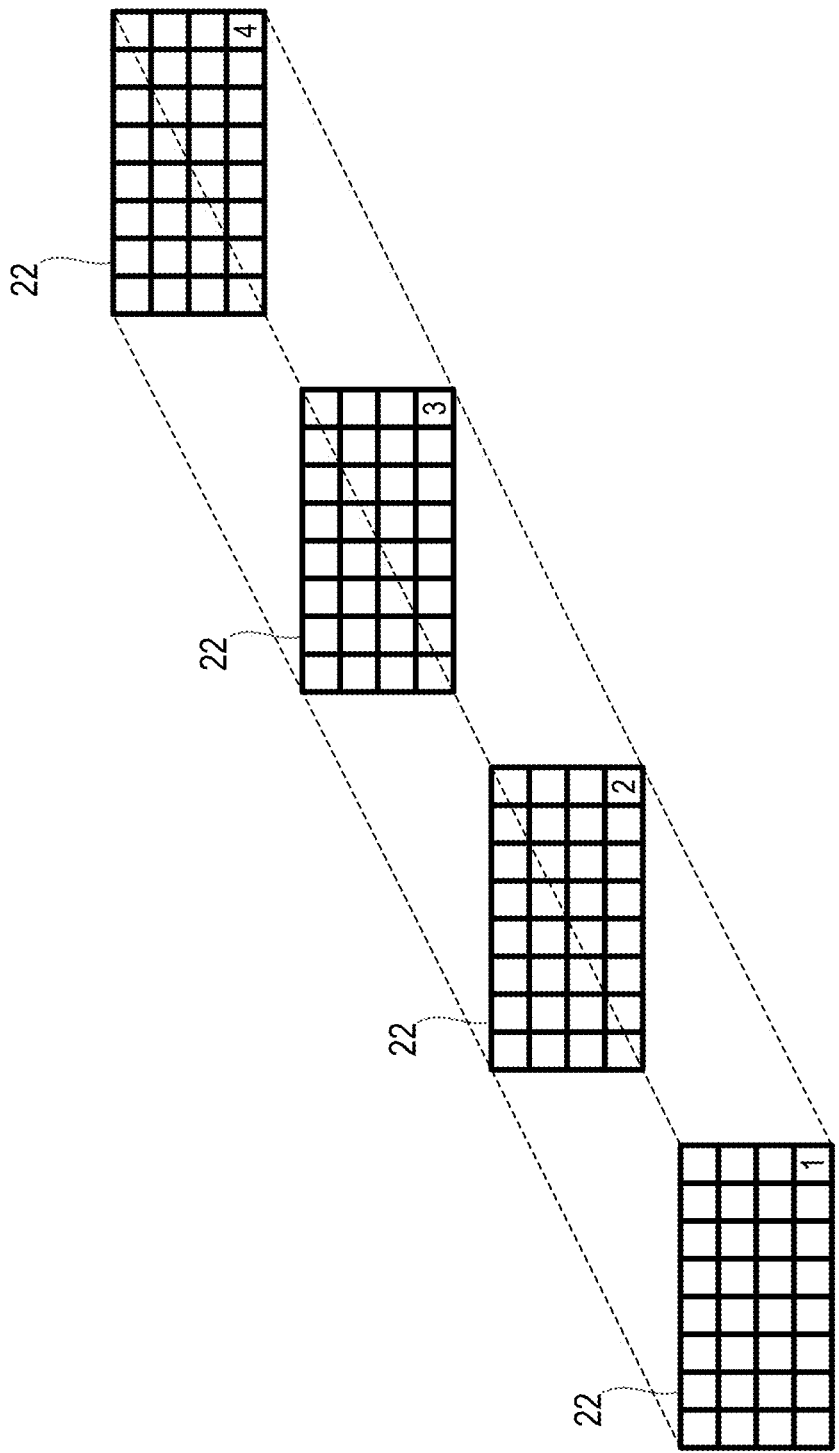

Next, each of the image frames 20 is divided into a plurality of frame segments 22 (step 103). Each frame segment 22 is a group of neighboring pixels in the image frame 20. An exemplary segmentation is illustrated in FIG. 4(b) in which each frame 20 is divided into equal-sized squares or rectangles. In alternative embodiments, the segments can be a different shape, such as triangular. In other (preferred) alternative embodiments, the shape of the segments 22 can be determined by the image in the image frame 20 (for example the boundaries of the shapes can follow boundaries between different colors in the image frame). In each embodiment, however, it will be appreciated that each frame segment 22 comprises a group of spatially-related (i.e. neighboring) pixels in each image frame 20. In the preferred embodiment, the frame segments 22 are also known in the art as 'super pixels', for example as described in "SLIC Superpixels Compared to State-of-the-art Superpixel Methods" by Achanta et al., IEEE Transactions on Pattern Analysis & Machine Intelligence 2012 vol. 34 Issue No. 11, November 2012: pp: 2274-2282.

In the preferred 'super pixel' embodiment in which the grouping of pixels/shape of the segments 22 is determined by the content of the image frame, the frame segments 22 can be determined by grouping pixels in the image frame 20 based on color and spatial similarities of the pixels. In this way, neighboring or closely neighboring pixels having a similar or consistent color will be grouped together into a single frame segment 22.

In the above embodiments, an image frame 20 is divided into frame segments 22 based solely on an analysis of that image frame 20. However, it is possible in some embodiments to divide a particular image frame 20 into frame segments 22 based on an analysis of that image frame 20 and one or more subsequent image frames 20. In other words, the spatial and/or color based segmentation of an image frame 20 described above is extended into the time domain so that pixels sharing appearance (e.g. color) and spatial similarities in the temporal domain are grouped together.

After segmenting the image frames 20, a plurality of video sub-sequences are formed from the frame segments 22 (step 105). In some cases, each video sub-sequence can comprise a frame segment 22 from each of the image frames 20. In other cases, a video sub-sequence can comprise a frame segment 22 from each image frame 20 in a subset of the image frames 20 in the video sequence, with the subset comprising two or more (preferably consecutive) image frames 20. In yet further cases, a video sub-sequence can comprise frame segments 22 from multiple subsets of image frames 20 concatenated together (with each subset comprising two or more image frames 20). In the embodiments where a video sub-sequence comprises a frame segment 22 from each of a subset of image frames 20 in the video sequence (for example a frame segment 22 from 2-9 image frames 20), the video sub-sequence is also referred to herein as a voxel.

Figure 4C:
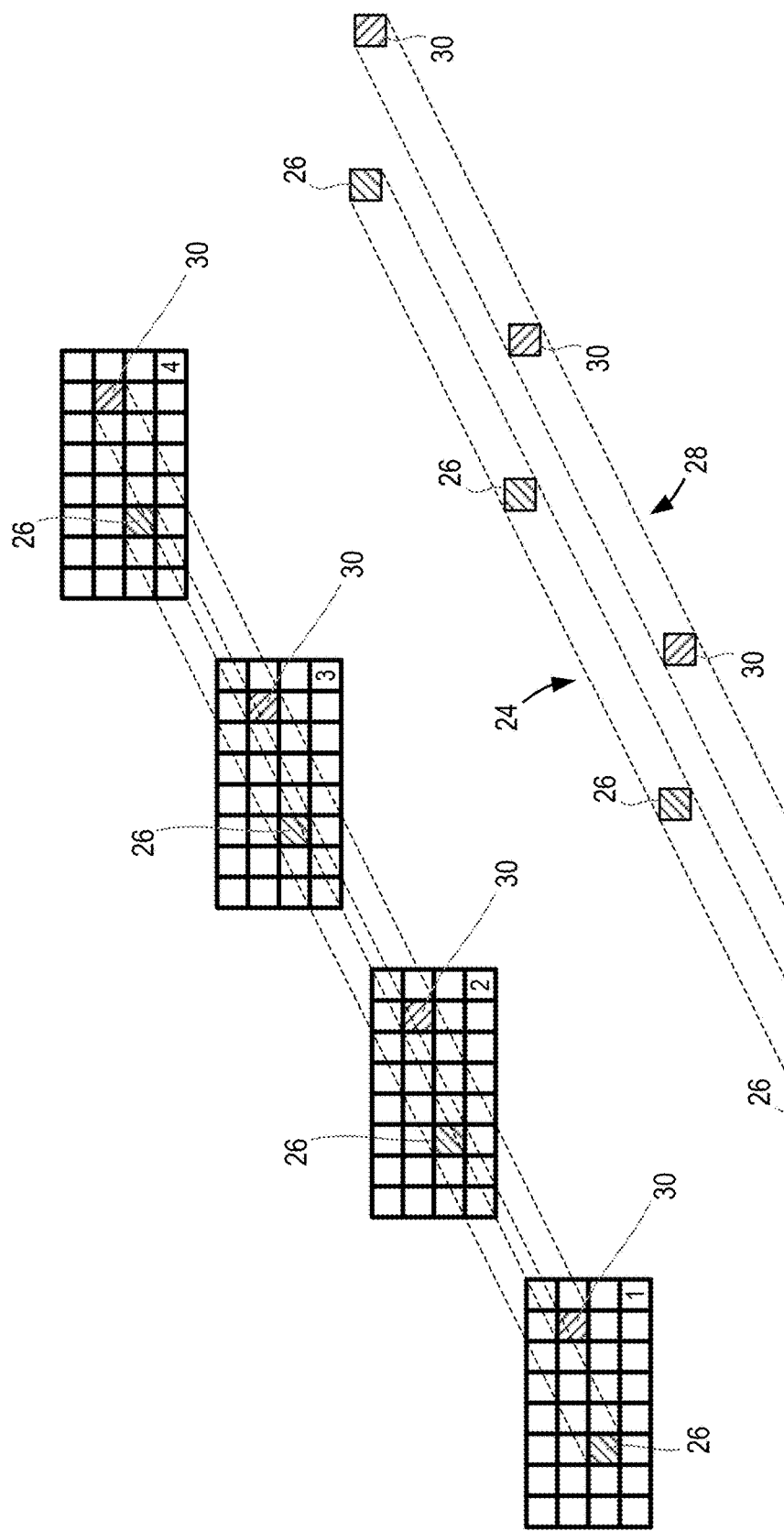

In some embodiments, a video sub-sequence is formed using frame segments 22 in the same spatial position within each image frame 20 in the video sequence or within each image frame 20 in the subset of the image frames 20, as appropriate. For example, one video sub-sequence can be formed from the frame segment 22 in the top left corner of the image frames 20, another from the frame segment 22 in the bottom left corner of the image frames 20, and so on. This is illustrated in FIG. 4(c) for two particular frame segments 22 in each of the four image frames 20. Thus, a first video sub-sequence 24 is formed from a first frame segment 26 in the same spatial position in each of the image frames 20 and a second video sub-sequence 28 is formed from a second frame segment 30 in another spatial position in each of the image frames 20.

However, in a preferred embodiment (which is particularly preferred when the frame segments 22 are formed by grouping pixels according to color and spatial similarities), to improve the robustness of the method to changes in the content of the video sequence (for example due to a subject moving), a video sub-sequence can be formed by selecting frame segments 22 from the image frames 20 that are consistent with each other (for example generally consistent in spatial location within the image frame and generally consistent in color). This can lead to the video sub-sequence 'winding' its way through the image frames 20 so that the video sub-sequence contains frame segments for a particular part of a subject (for example as a subject moves from left to right in the video sequence, a particular video sub-sequence can be formed by a frame segment 22 in each image frame that corresponds to the subject's cheek due to spatial and color similarities). One preferred way to form the video sub-sequences is, for a particular frame segment 22 in an image frame 20, to identify the frame segment 22 in the next image frame 20 that has the minimum chromatic energy (i.e. minimum difference in chrominance) and spatial-distance energy (i.e. minimum spatial-distance) from the particular frame segment 22. It will be understood that chromatic energy refers to an energy function based on the chrominance values of the pixels in the frame segment 22 and a frame segment 22 in the next image frame 20, and thus minimizing the chromatic energy to form a video sub-sequence can comprise, for a particular frame segment 22, identifying the frame segment 22 in the next image frame 20 that has the smallest chromatic energy to the frame segment 22 under consideration. It will be appreciated that the more different the chrominance for the pixels in a frame segment 22 compared to the chrominance for the pixels in the frame segment 22 under consideration, the higher the chromatic energy, and thus the lower the likelihood that the frame segment 22 will be selected for that video sub-sequence. It will also be understood that spatial-distance energy refers to an energy function based on the spatial-position of the frame segment 22 in the image frame 20 and the spatial-position of the frame segment 22 in the next image frame 20, and thus minimizing the spatial-distance energy to form a video sub-sequence can comprise, for a particular frame segment 22, identifying the frame segment 22 in the next image frame 20 that provides the smallest spatial distance in the frame segment 22 under consideration. It will be appreciated that the larger the distance from the position of a frame segment 22 in the next image frame 20 to the position of the frame segment 22 under consideration, the higher the spatial-distance energy, and the lower the likelihood that the frame segment 22 will be selected for that video sub-sequence. In an alternative approach, it is also possible to initialize the new voxels at time t using the centers of the voxels at time t−1. In cases where the voxels overlap in time, the center in the last frame segment 22 of a voxel determines the center in the first frame segment 22 of the next voxel.

Each video sub-sequence is then analyzed to determine a pulse signal for each video sub-sequence (step 107). The pulse signal represents the color, or changes in the color, of the frame segments 22 in a video sub-sequence. Various techniques for determining a pulse signal from a video sequence (and thus a video sub-sequence) are known in the art and will not be described in detail herein. However, some exemplary techniques are mentioned in the description of the Voxel-Pulse-Spectral (VPS) method presented below.

In some embodiments, the pixel values (e.g. RGB values) of each frame segment 22 are averaged, and the pulse signal formed from a time series of the average value for each frame segment 22 in the sub-sequence. In some embodiments, the pixel values are weighted based on the spatial position of the pixel in the frame segment 22 and/or a difference in color with a pixel or group of pixels at or near the center of the frame segment 22, and the average of the weighted values determined. For example the pixel values can be weighted based on the distance from the pixel to the spatial boundary of the frame segment 22, and/or the distance from the pixel to the center of the frame segment 22. Preferably the weighting leads to the pixels close to the segment 22 boundary being less weighted as they are less reliable than pixels close to the middle of the segment 22 due to jittering artifacts between neighboring segments 22.

Figure 4D:
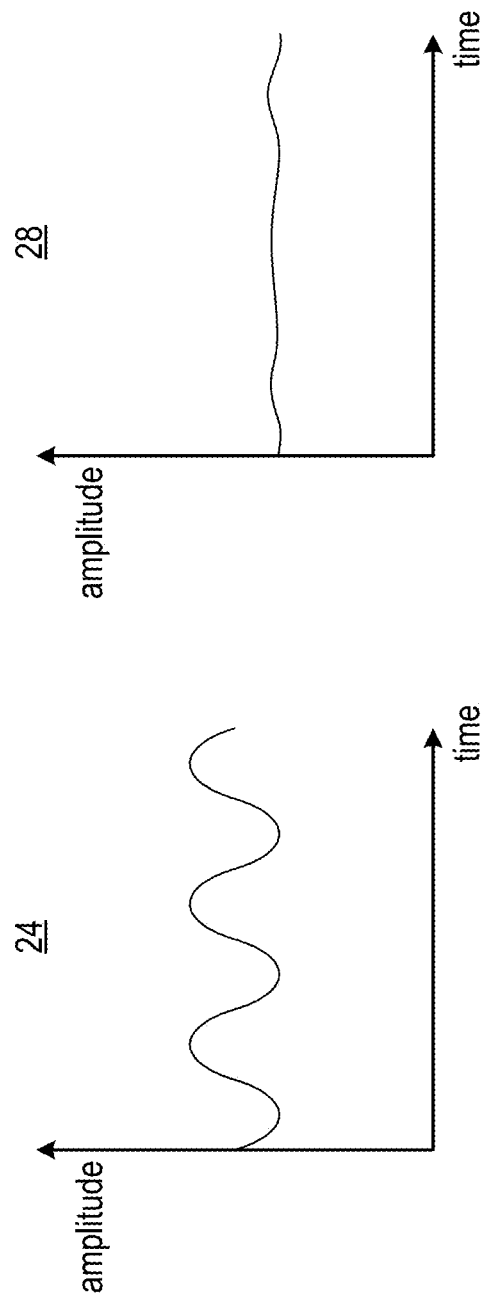

Exemplary pulse signals are shown in FIG. 4(d) for the two video sub-sequences 24, 28. In this example, the video sub-sequence 24 contains an area of living skin tissue, and therefore the pulse signal determined from this video sub-sequence will exhibit characteristics typical of a PPG signal (i.e. varying in amplitude consistent with changes in blood perfusion in the skin of the subject due to the beating of the heart). The video sub-sequence 28 does not contain an area of living skin tissue, and therefore the pulse signal determined from this video sub-sequence will not exhibit characteristics that are typical of a PPG signal (and, in the absence of changes in the ambient lighting in the video sequence, the pulse signal for sub-sequence 28 may correspond generally to a noise signal).

Once a pulse signal is determined for each video sub-sequence a similarity matrix is determined for the video sequence (step 109). The similarity matrix is a matrix in which similar pulse signals are mutually correlated. The use of a similarity matrix is advantageous as it does not require any parameters to be predefined (e.g. parameters based on skin tone or clustering).

The similarity matrix is preferably formed by determining pairwise similarities for each pulse signal with the other pulse signals. That is, for each pulse signal, a measure of the similarity with each of the other pulse signals is determined. These pairwise similarity measures are then combined to form the similarity matrix.

The pairwise similarity measures preferably include or are frequency-based pairwise similarity measures. This is advantageous since different frame segments 22 corresponding to areas of living skin tissue of the same particular subject should exhibit pulse signals that have similar (or the same) frequency peak index, phase or a low entropy in the correlation.

The measure of pairwise similarity for a pulse signal and one of the other pulse signals can be a measure of the correlation between at least part of the frequency spectra of the pulse signal and the one of the other pulse signals (which is referred to herein as the spectrum peak), a measure of the normalized cross-correlation between at least part of the frequency spectra of the pulse signal and the one of the other pulse signals (which is referred to herein as the spectrum phase), a measure of the regularity of correlation between at least part of the frequency spectra of the two pulse signals (which is referred to herein as the spectrum entropy) and/or the result of an inner product of the two pulse signals (which can optionally be filtered before the inner product is calculated). Further details of these pairwise similarity measures can be found in the description of the VPS method below.

Those skilled in the art will be aware of alternative or further measures of pairwise similarity to those presented above that can be determined and used to form a similarity matrix.

In some embodiments, multiple measures of pairwise similarity (e.g. spectrum peak and spectrum phase) can be determined for each pulse signal with each of the other pulse signals, and those measures combined to form a distance metric representing the pairwise similarity for each pulse signal with each of the other pulse signals. The similarity matrix can then be determined based on the distance metrics.

Once the similarity matrix is determined, areas of living skin tissue are identified in the video sequence from the similarity matrix (step 111). The areas of living skin tissue are identified by performing matrix decomposition of the similarity matrix. In some embodiments, the matrix decomposition can by singular value decomposition (SVD), QR decomposition, sparse SVD, incremental SVD, principal component analysis, PCA, or independent component analysis, ICA. These techniques are generally known in the art and will not be described in detail herein. In a preferred embodiment, which is described in more detail below, the similarity matrix is decomposed using incremental sparse PCA.

Step 111 can comprise factorizing (decomposing) the similarity matrix into orthogonal bases to find the parts of the video sequence belonging to the same subject. This factorizing results in different kinds of similarities being separated into independent directions. This results in the frame segments 22 belonging to the same subject being clustered in the same direction.

Although not shown in FIG. 3, once areas of living skin tissue have been identified in the video sequence, one or more physiological characteristics of the subject (the subject with the identified living skin tissue) can be determined from the video sequence.

In some embodiments, the physiological characteristic(s) can be determined from the one or more pulse signals associated with the identified areas of living skin tissue. In this case, the one or more pulse signals can be individually analyzed to determine a physiological characteristic and the physiological characteristics combined (e.g. averaged) to give an overall measure of the physiological characteristic for the subject. Alternatively the one or more pulse signals can be combined (e.g. averaged) to give a single pulse signal, and the pulse signal analyzed to determine a physiological characteristic.

In other embodiments, the video sequence can be re-processed to extract a pulse signal or signals from the areas identified to be living skin tissue, and that pulse signal(s) processed to determine the physiological characteristic.

The pulse signal(s) derived from the video sequence are similar to signals obtained using a PPG sensor, so the one or more physiological characteristics of the subject can include any characteristic that can be derived from a PPG signal or other measure of the blood perfusion (or changes in the blood perfusion) of the subject, such as heart rate, heart rate variability, beat-to-beat interval, breathing rate, breathing signal, SpO2 value (i.e. the arterial oxygenation level of the blood), etc. Thus, techniques known in the art for deriving such physiological characteristics from PPG signals (e.g. peak detection in the frequency domain for determining heart rate) can be used to derive values for physiological characteristics from the pulse signal(s) obtained from areas identified to be living skin tissue.

A preferred embodiment of the techniques described herein is set out below, and is referred to herein as the Voxel-Pulse-Spectral (VPS) method.

Voxel-Pulse-Spectral (VPS) Method

Camera-Based Pulse Extraction

In the human cardiovascular system, blood pulses propagating throughout the body changes the blood volume in skin tissue. Since the optical absorption of haemoglobin in blood varies across the light spectrum, detecting color variations of skin reflection can reveal the pulse rate. Recent remote photoplethysmography (rPPG) techniques enable the detection of pulse-induced color variations on human skin using a regular RGB camera. Blind Source Separation methods (e.g. PCA-based and ICA-based) have been proposed to factorize the temporal RGB signals for finding the pulse. A Chrominance-based rPPG method has also been proposed to define the pulse as a linear combination of RGB channels under a standardized skin-tone assumption, which is one of the most accurate rPPG methods in dealing with realistic challenges (e.g. different subject skin colors).

Pulse-Based Region of Interest Detection

Given the fact that the human pulse can be measured by rPPG in video sequences, the pulse signal can thus be used to assist the subject detection, i.e. detecting alive subjects by locating their living skin tissue. An existing technique proposes a face detection method based on the pulse signal which slices the video into fixed rigid-grids for local pulse extraction. It sets a hard threshold to find the grids with a high spectrum energy and label them as the face region. It is limited to videos in which the stationary face needs to be placed at a pre-defined distance from the camera. The VPS method described herein does not suffer from these limitations. In another existing technique, an optimal Region of Interest (RoI) selection method on the face to enhance the rPPG monitoring was proposed. However, the RoI is constrained to predefined facial landmarks, which is not a general solution for subject detection, i.e. it cannot detect other body parts (e.g. hands) that might be visible in a video. In contrast, the VPS method described herein does not make such an assumption and can detect all body parts with pulsatile blood volume.

Figure 5:
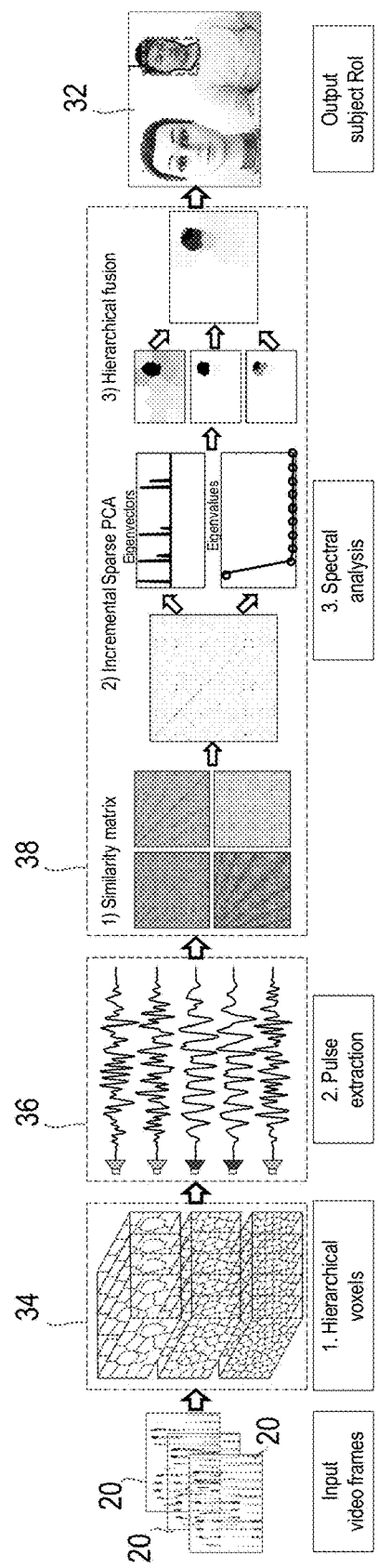
FIG. 5 is a diagram illustrating the processing stages in the exemplary Voxel-Pulse-Spectral method.

An overview of the VPS method is shown in FIG. 5, which takes an input video sequence comprising image frames 20 and outputs the subject RoI 32 (i.e. the areas of the video sequence that correspond to living skin tissue). Consistent with the method shown in FIG. 3, the video sequence is segmented into a plurality of sub-sequences (hierarchical voxels stage 34—steps 103 and 105), pulse signals are determined for each sub-sequence (pulse extraction stage 36—step 107), a similarity matrix is determined and analyzed to identify RoIs (spectral analysis stage 38—steps 109 and 111). Each stage is discussed in detail below.

Hierarchical Voxels

Given a video sequence without any prior information about the subject (or about the content in general), the video sequence is first segmented into dense local regions where a pulse can be independently measured (this is the hierarchical voxels stage 34 in FIG. 5). Although the video sequence can be sliced into fixed rigid-grids, this means that the subject size is quantized by the grid geometry, which struggles or fails when the subject is small or when there is body motion. Therefore, in the VPS method, it is preferred to use a superior video segmentation method for pulse extraction which is called 'hierarchical voxels'. The hierarchical voxels consist of spatiotemporally coherent clusters (frame segments), preferably in multiple scales (with the scale determining the number of clusters/segments that each image frame 20 is divided into), where pixels in image frames 20 sharing appearance and spatial similarities in the temporal domain are grouped together. Although multiple scales are preferred and used in the following description of the VPS method, it is possible to use a single scale in the VPS method.

Starting from one scale, constructing the voxels (video sub-sequences that comprise a frame segment from a subset (e.g. 2, 3, 4, etc.) of consecutive image frames) is defined as the procedure of minimizing the chromatic energy $E_c$ (i.e. minimizing the difference in chrominance for the frame segments) and spatial-distance energy $E_s$ (i.e. minimizing the difference in spatial distance between the frame segments) between temporally-adjacent superpixels/frame segments in a short interval $T \in \{2n+1, n \in \mathbb{N}^+\}$ as:

$$\operatorname*{argmin}\left(\sum_{t-\frac{T-1}{2}}^{t+\frac{T-1}{2}} \sum_{p \in P(t)} (1-\lambda)E_c^t(p, k) + \lambda E_s^t(p, k)\right), \quad (1)$$

where $p \in P(t)$ is the set of pixels in the t-th frame. The representation of p is a 4-dimensional feature vector (x, y, u, v), where (x, y) and (u, v) are respectively the coordinates in the image plane and the chromatic plane (e.g. UV plane of YUV space, the empirical space for skin segmentation). K-means clustering is performed to assign pixels into k clusters for minimizing the total energy during T. $\lambda$ is the parameter controlling the balance between two energy terms.

Furthermore, the single scale voxels are extended to multiple scales by initializing different k in equation 1 simultaneously, where each scale is an independent clustering. Considering that the voxels in separate scales have different resolutions and energy variations, the $\lambda_i$ in i-th scale is adaptively self-tuned based on its own energy variations at t as:

$$\lambda_i^t = \log(k) \sqrt{\frac{\sigma(\phi(u_i^t)) \cdot \sigma(\phi(v_i^t))}{\sigma(\phi(x_i^t)) \cdot \sigma(\phi(y_i^t))}}, \quad (2)$$

where $\sigma(\bullet)$ denotes the standard deviation operator; $\phi(\bullet)$ represents the set of cluster means; log(k) controls the voxel compactness, i.e. voxels with higher resolution (larger k) should be more compact. The real-time tuning of $\lambda$ in different scales avoids volatile and flickering clustering, which preserves the fine-grained segmentation.

Figure 1:
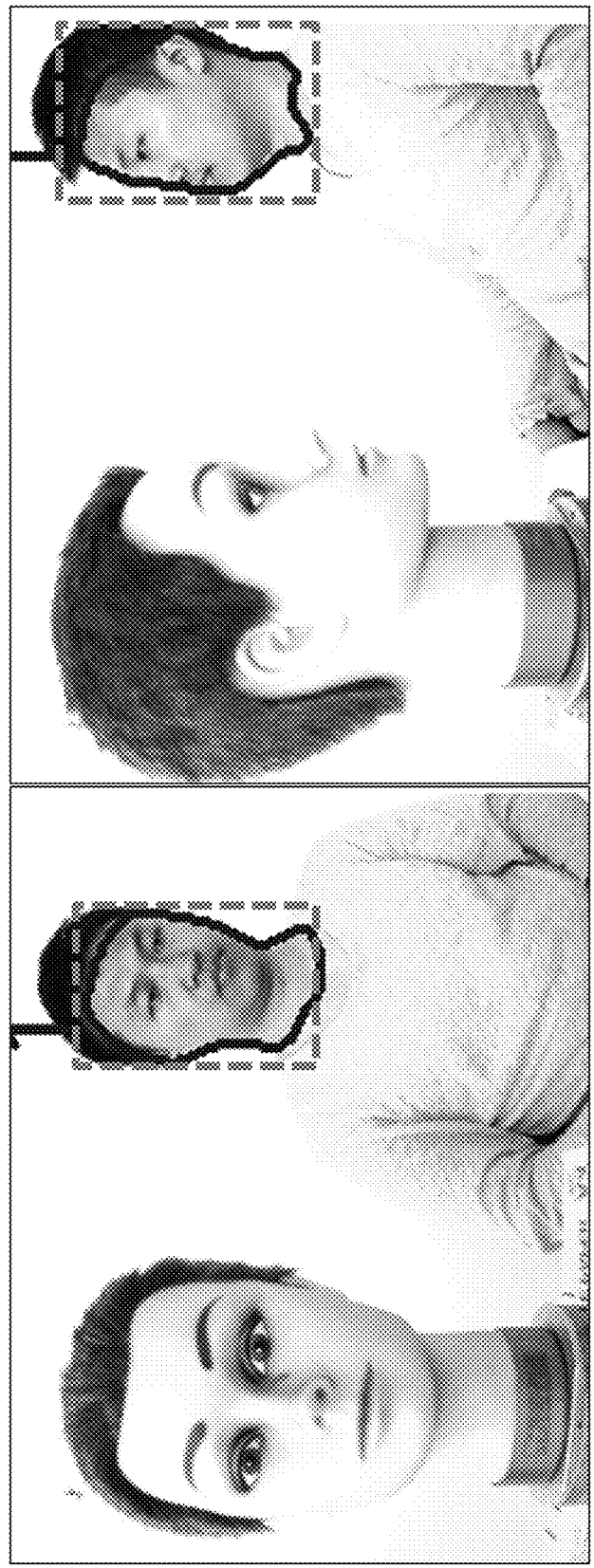
FIG. 1 illustrates the desired operation of a living skin tissue detection technique.
Figure 6:
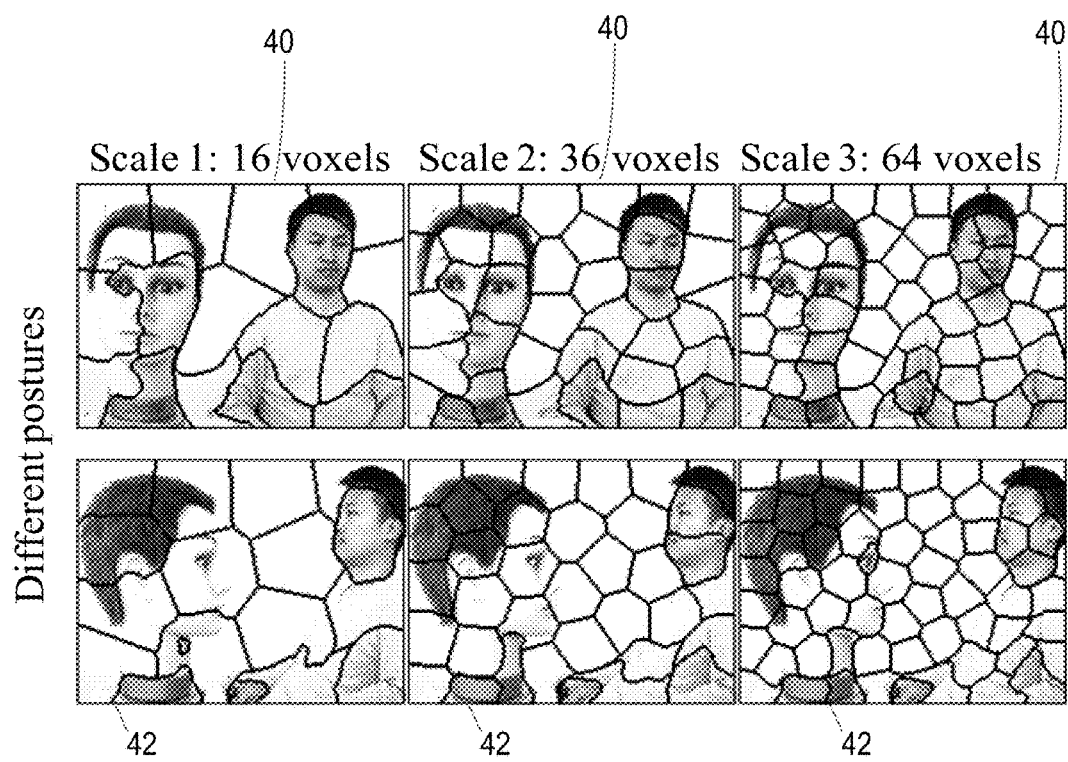
FIG. 6 illustrates segmentation of an image frame in three different scales.

There are four benefits of using hierarchical voxels as described above, as illustrated in FIG. 6, which shows three different resolutions/scales (k=16, k=36; k=64) for two different images comprising a live subject and an artificial face. In FIG. 6, the first image 40 corresponds to the left hand image in FIG. 1 and shows a human face and an artificial face that are both facing the camera. The second image 42 corresponds to the right hand image in FIG. 1 and shows a human face and artificial face side on to the camera. Firstly, using hierarchical voxels establishes the spatio-temporally coherent "tubes" (video sub-sequences) for pulse measurement. Secondly, it enables the scale-invariant subject detection in a video. Thirdly, it maintains high boundary recall of subject shapes (as indicated by the boundaries of the frame segments following shapes in the image. Fourthly, it creates a statistical observation of skin-regions, since the pulse measured from voxels with different resolutions have different quantized qualities.

Pulse Extraction

This section describes pulse extraction stage 36 in FIG. 5. Each voxel (i.e. video sub-sequence) in the hierarchy is assumed to be an independent pulse sensor in parallel pulse extraction. In a preferred embodiment, the Chrominance-based method (CHROM) is used for pulse measurement, which is described in "Robust pulse rate from chrominance-based rPPG" by G. de Haan and V. Jeanne, TBME, 60(1): 2878-2886, 2013. However, those skilled in the art will be aware of other techniques that can be used to determine the pulse signal for a voxel. For example, as noted above, techniques based on PCA or ICA can be used to extract a pulse signal from a voxel, or the "PBV" method as described in "Improved motion robustness of remote-PPG by using the blood volume pulse signature" by G. de Haan and A. van Leest, Physiol. Meas. 35 1913, 2014, can be used to extract a pulse from RGB traces. Different from CHROM that uses the spatially averaged RGB of all pixels to derive the pulse signal in a local region/cluster, the pixel RGB values in a voxel are combined by weighting them based on their distance to the voxel boundary, i.e. pixels close to the voxel boundary are less reliable due to occasional uttering artifacts between neighboring voxels and thus should be less weighted. Assuming that the closest Euclidean distance from a pixel k to the voxel boundary is $d_k$, the average RGB of j-th voxel in i-th scale at t is combined as:

$$(\overline{R}_{ij}^t, \overline{G}_{ij}^t, \overline{B}_{ij}^t) = \frac{\sum_{k=0}^{N}(d_k \cdot (R_{ijk}^t, G_{ijk}^t, B_{ijk}^t))}{\sum_{k=0}^{N} d_k}, \quad (3)$$

where N denotes the number of pixels in j-th voxel. In a constant lighting environment, human skin tissue shows the same relative PPG-amplitude, but the chromatic differences in voxels lead to the variations in pulse-amplitudes. So different from CHROM, the temporal derivatives of average RGB in a voxel are used, i.e. $dC_{ij}^t = C_{ij}^t - C_{ij}^{t-1}$, $C \in \{\overline{R}, \overline{G}, \overline{B}\}$ to derive its chrominance-signals. In the interval T (defined in equation 1), the normalized chrominance derivatives are calculated as:

$$\begin{cases} \overrightarrow{dX}_{ij}^T = 3 \frac{\overrightarrow{dR}_{ij}^T}{\sum_{t=0}^{T} dR_{ij}^t} - 2 \frac{\overrightarrow{dG}_{ij}^T}{\sum_{t=0}^{T} dG_{ij}^t} \\ \overrightarrow{dY}_{ij}^T = 1.5 \frac{\overrightarrow{dR}_{ij}^T}{\sum_{t=0}^{T} dR_{ij}^t} + \frac{\overrightarrow{dG}_{ij}^T}{\sum_{t=0}^{T} dG_{ij}^t} - 1.5 \frac{\overrightarrow{dB}_{ij}^T}{\sum_{t=0}^{T} dB_{ij}^t} \end{cases}, \quad (4)$$

where $(dR_{ij}^t, dG_{ij}^t, dB_{ij}^t)$ denotes the temporal derivatives of RGB in a voxel between two image frames. The chrominance derivatives estimated in each interval are linearly combined into pulse derivatives and further integrated. Afterwards, different pulse intervals are overlap added to a complete pulse-signal $\vec{S}_{ij}^L$ with length L. This procedure is interpreted as:

$$\vec{S}_{ij}^L = \sum_{t=0}^{L-T+1} \vec{S}_{ij}^{t+T} + w \cdot csum\left(\overrightarrow{dX}_{ij}^T - \frac{\sigma(\overrightarrow{dX}_{ij}^T)}{\sigma(\overrightarrow{dY}_{ij}^T)} \overrightarrow{dY}_{ij}^T\right), \quad (5)$$

where csum(•) denotes the cumulative sum of temporal derivative signals; w is the Hanning window for smoothing the overlap adding. Consequently, the parallel extracted pulse-signals $\vec{S}_{ij}^L$ (from j-th voxel in i-th scale) are centralized and normalized as:

$$\vec{S}_{ij}^L = \frac{\vec{S}_{ij}^L - \mu(\vec{S}_{ij}^L)}{\sigma(\vec{S}_{ij}^L)}, \quad (6)$$

where μ(•) denotes the averaging operation. Note that the pulse-signal is the only feature used in this method. No other appearance features like color or texture are used.

Spectral Analysis

This section describes spectral analysis stage 38, which comprises three sub-stages, forming a similarity matrix, performing incremental sparse PCA on the similarity matrix, and using hierarchical fusion to identify areas of living skin tissue in the video sequence.

It has been noted that pulse signals extracted from skin regions belonging to the same subject share similarities in many aspects such as phase and frequency, whereas the ones extracted from non-skin regions (e.g. background) are random noises without correlation. Therefore, after extracting the pulse signals from hierarchical voxels, pairwise similarities of pulse signals are used to find alive subjects. This is also applicable to the case of multiple subjects in the video sequence, because the pulse measured from different subjects can be differentiated in phase and frequency as well.

Similarity Matrix—

In this step, a similarity matrix Σ=(D,C) is created to interconnect the hierarchical voxels based on the measured pulse. In Σ, the entries D in the diagonal trace contain all voxels in different scales; the remaining entries C denote the pairwise connection between any pair of voxels. To build such a similarity matrix, the distance metric for measuring the pulse similarity needs to be defined. The most commonly used distance metrics, i.e. L1 and L2 distances, are not applicable to the pulse feature. However, compared to other appearance features (e.g., Haar, in P. Viola and M. Jones, "Rapid object detection using a boosted cascade of simple features", CVPR, 2001, 1" and HOG, in N. Dalal and B. Triggs, "Histograms of oriented gradients for human detection", CVPR, 2005, 1), an essential and unique character in the pulse feature is that it contains periodicity. It has been noted that pulse signals from the same subject show the following relations: (1) they have similar frequency and thus their cross-correlation presents a significant spectrum peak; (2) they have no significant phase shift; (3) their frequency correlation is regular and less disordered; and (4) if considering pulse signals as multidimensional vectors, the included angle between two similar vectors is small. Therefore, a preferred distance metric used to build the similarity matrix for pulse signals emphasizes the above connections, and is composed of four different measurements:

Spectrum peak—In the frequency domain, a pulse-rate band f∈[40, 240] BPM (Beats Per Minute) is defined for voxels to communicate, which is a broad range for healthy subjects including neonates and sporting subjects. The spectrum peak of two cross-correlated pulse-signals is defined as:

$$F = \arg\max_{f \in [40, 240]} \left( \mathcal{F}(\vec{S}_{ij}^L) \cdot \mathcal{F}(\vec{S}_{i'j'}^L)^* \right), \quad (7)$$

where ○ denotes the element-wise product; * is the conjugation; F(•) represents the Fast Fourier Transform (FFT).

Spectrum phase—Two similar pulse signals are also in the same phase, so their normalized cross-correlation should show a strong response in the time domain as:

$$P = \max(\mathcal{F}^{-1}(NCC)), \quad (8)$$

with $$NCC \frac{\mathcal{F}(\vec{S}_{ij}^L) \cdot \mathcal{F}(\vec{S}_{i'j'}^L)^*}{\left\| \mathcal{F}(\vec{S}_{ij}^L) \cdot \mathcal{F}(\vec{S}_{i'j'}^L)^* \right\|_2}, \quad (9)$$

where $\|\cdot\|_2$ is the L2-norm; $\mathcal{F}^{-1}(\cdot)$ denotes the inverse FFT.

Spectrum entropy—The term "entropy" is used to measure the regularity of correlation between two pulse-signals as:

$$E = \frac{\sum_{f=40}^{240} NCC(f)\log(NCC(f))}{\log(240-40)}, \quad (10)$$

where the interpretation of E is consistent with the other measurements, i.e. larger E denotes better correlation.

Inner product—In the time domain, we use the inner product to measure the cosine angle between two pulse-signals as:

$$I = \left\langle \frac{\vec{S}_{ij}^L}{\|\vec{S}_{ij}^L\|_2}, \frac{\vec{S}_{i'j'}^L}{\|\vec{S}_{i'j'}^L\|_2} \right\rangle, \quad (11)$$

where $\langle,\rangle$ denotes the inner product operation.

Figure 7:
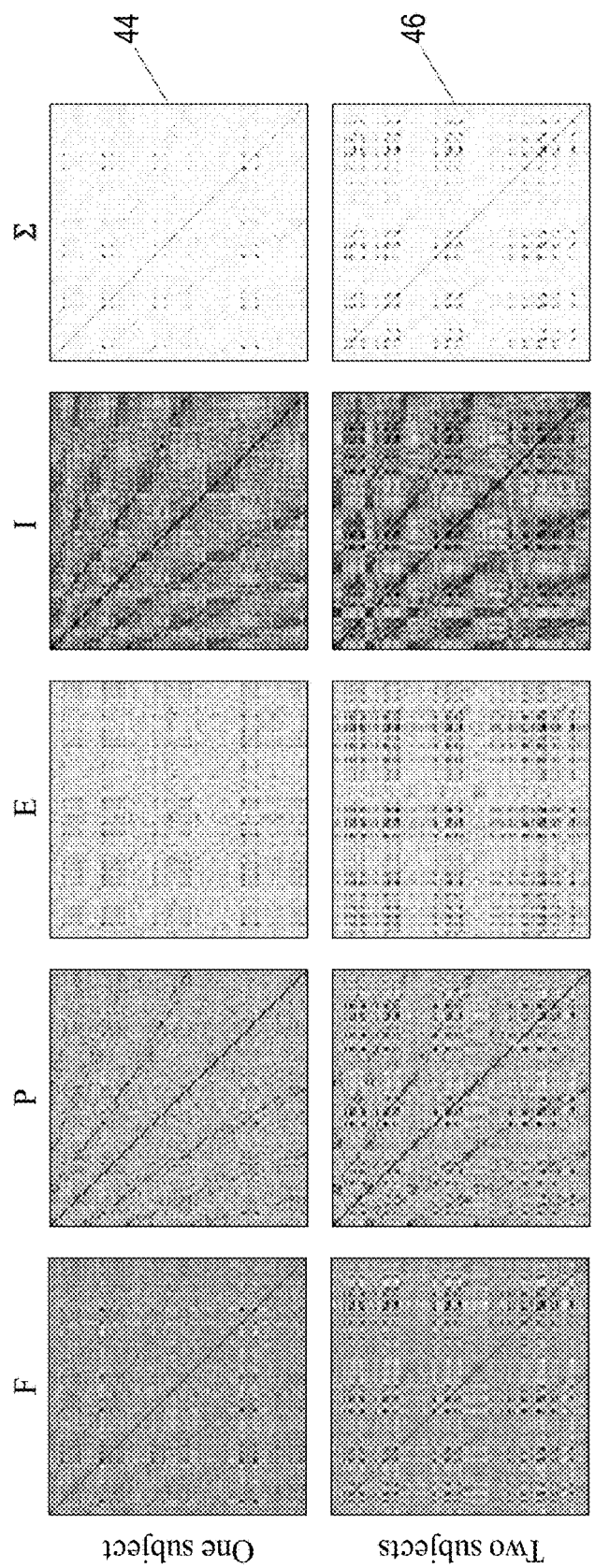
FIG. 7 illustrates four different measures of pairwise similarity and a resulting similarity matrix.

Finally, these four measurements are normalized to the range [0; 1] and fused together with a Gaussian kernel as:

$$\sum = 1 - \exp\left(-\frac{(F \cdot P \cdot E \cdot I)^2}{2\sigma_{I,F,P,E}^2}\right), \quad (12)$$

where σI, F, P, E represents the entry-wise standard deviation between four matrices. It should be noted that the four measurements are not completely independent from each other, the redundancy between measurements is beneficial for reducing the uncertainty in similarity estimation. FIG. 7 shows an example of four measurements and their fused similarity matrix Σ 44, 46 for two video sequences, one that includes a single living subject, and the other including two living subjects. The entries with higher energy represent the index of similar voxels in the hierarchy.

In the distance metric used herein, two well-aligned pulse signals show boosted frequency energy during the cross correlation, which can effectively suppress the noise entries (e.g. voxels without pulse). In contrast, previous distance metrics are all objective measurements that cannot enhance the connection between similar entries in the comparison. In the end, all voxels in the hierarchy are mutually connected in the similarity matrix. The task of detecting an alive subject in voxels can be reformulated as finding a subspace partition of the similarity matrix such that the entries in the same subspace have identical similarity direction.

Incremental Sparse Matrix Decomposition—

The similarity matrix Σ 44, 46 can be interpreted as a linear combination of $\lambda_1 x_1 x_1^T + \lambda_2 x_2 x_2^T + \ldots \lambda_n x_n x_n^T$, where $x_i \in X$ is a set of orthogonal vectors in the multi-dimensional space. In order to find the voxels belonging to the same subject, a matrix decomposition technique is used to factorize Σ into X, where different subjects are separated into different eigenvectors. Since Σ is a sparse matrix with many zero entries (e.g. the voxels pointing at background share no similarity), sparse PCA is applied to decompose Σ into X by seeking a trade-off between expressive power and data interpretability.

Sparse PCA is described in "Sparse PCA: Convex relaxations, algorithms and applications" by Y. Zhang, A. d'Aspremont and L. Ghaoui, International Series in Operations Research & Management Science Volume 166:915-940, 2012. The Sparse PCA finds the first sparse eigenvector with the maximum variance in Σ by optimizing the following non-convex objective function:

$$\underset{X}{\operatorname{argmax}}(X^T \Sigma X) \text{ subj. to } \|X\|_2 = 1, \|X\|_1 \leq n, \quad (13)$$

where $\|\cdot\|_2$ is the L1-norm; n>0 controls the cardinality of X. However, computing sparse eigenvectors with maximum variance is a combinatorial problem and numerically hard to solve, so the non-convex rank constraint in equation 13 is dropped following the lifting procedure for semidefinite relaxation with $I_1$ penalization as:

$$\underset{\hat{\Sigma}}{\operatorname{argmax}} Tr(\Sigma\hat{\Sigma}) - \rho\|\hat{\Sigma}\|_1 \text{ subj. to } Tr(\hat{\Sigma}) = 1, \hat{\Sigma} \succeq 0, \quad (14)$$

where Tr(•) denotes the matrix trace operation; ρ>0 controls the sparsity; $\hat{\Sigma} = XX^T$ is a symmetric matrix approximated by the first leading eigenvector. At this point, an algorithm named Hybrid Conditional Gradient Smoothing (HCGS) can be used to solve equation 14. HCGS is described in "Hybrid conditional gradient-smoothing algorithms with applications to sparse and low rank regularization" by A. Argyriou, M. Signoretto and J. Suykens, arXiv preprint: 1404.3591, 2014. The merit of HCGS is the fast convergence in convex relaxation using conditional gradient approaches.

However in practice, Σ may consist of multiple sparse eigenbasis in case of multiple subjects, whereas equation 14 only promotes the sparsity in the first leading eigenvector. To address this issue, the succeeding sparse eigenvectors $x_i$ are estimated by sequentially deflating Σ with preceding sparse eigenvectors $x_1, x_2, \ldots, x_{i-1}$ using Hotelling's deflation as:

$$\Sigma_i = \Sigma_{i-1} - (x_i^T \Sigma_{i-1} x_i) x_i x_i^T, i \in [1, m], \quad (15)$$

with $$m = \underset{i}{\operatorname{argmax}}\left(\frac{x_{i-1}^T \sum_{i-1} x_{i-1}}{1 + x_i^T \sum_i x_i}\right), \quad (16)$$

where $x_i \in X$ can be derived by the power iteration in HGCS; m is the automatically found number of most expressive eigenvectors, which also implies the number of subjects in a video sequence, i.e. m is usually found at the largest eigenvalue gap.

Figure 8:
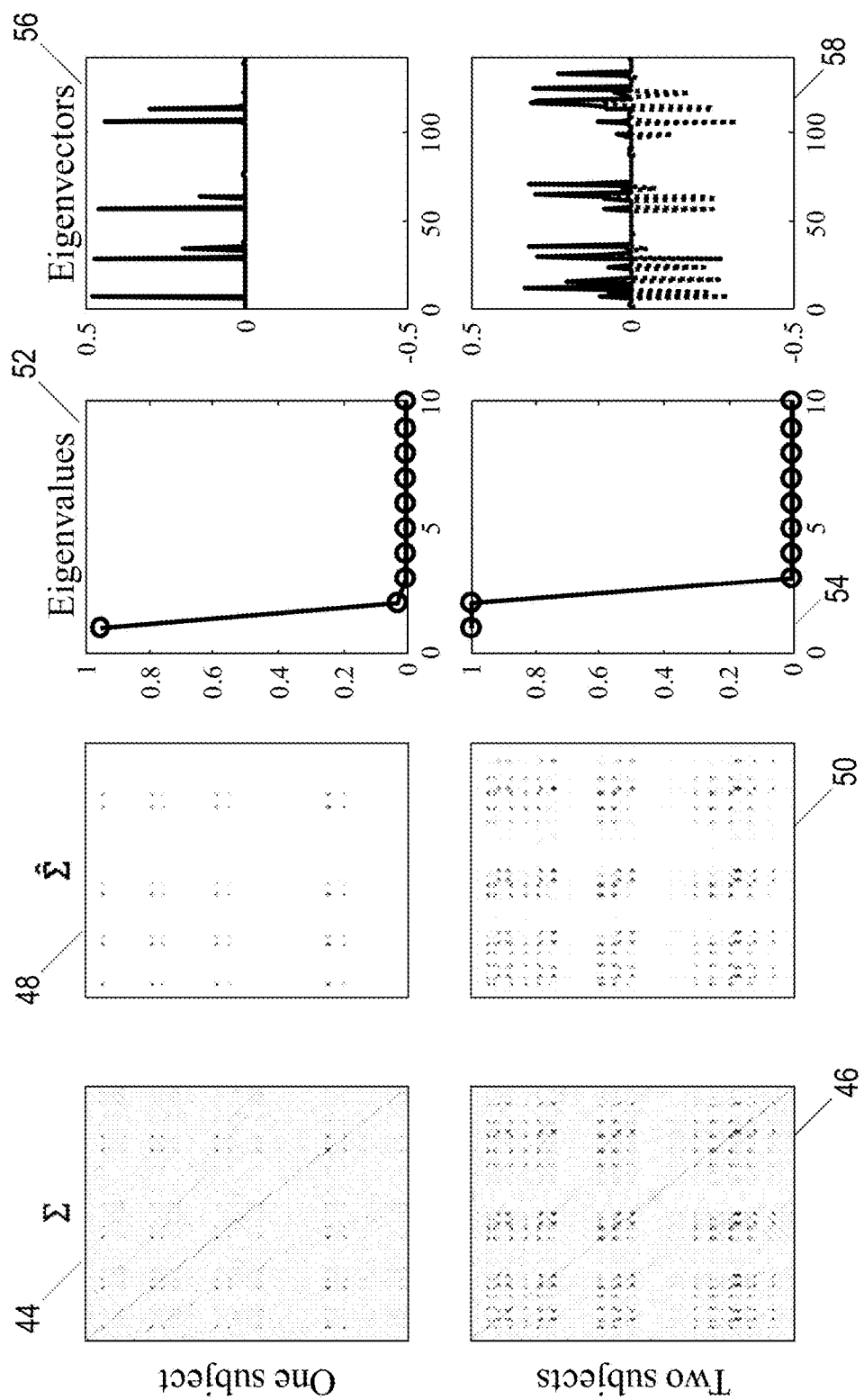
FIG. 8 shows an example of similarity matrix decomposition using incremental sparse PCA.

FIG. 8 shows an example of similarity matrix decomposition using incremental sparse PCA for the two similarity matrices 44, 46 shown in FIG. 7, where similar voxels are factorized into the same directions in the selected eigenvectors. Thus FIG. 8 shows the factorized and selected eigenbasis from a similarity matrix; the noisy entries in the original Σ 44, 46 are eliminated in $\hat{\Sigma}$ 48, 50; the eigenvalues (shown in graphs 52 and 54 respectively) clearly show the number of most expressive eigenvectors in $\hat{\Sigma}$ (shown in graphs 56 and 58 respectively).

As a matter of fact, some intrinsic (e.g. pulse rate variation) and extrinsic (e.g. luminance changes) factors may occasionally change the similarity matrix in subsequent frames, which leads to an instability of the sparse eigenvectors estimated from each single frame. To solve this problem, incremental subspace updating is employed to smoothly adapt the $x_i \in X$ to real-time changes in the time domain. Basically, it considers the time-varying similarity matrix $\hat{\tau}_{new}$ as a new observation, and use multiple observations $[\hat{\Sigma}_{old}, \hat{\Sigma}_{new}]$ from different frames to enrich the subspace model as:

$$[U, D, V] = SVD([\hat{\Sigma}_{old}, \hat{\Sigma}_{new}]) \quad (17)$$

where SVD(•) denotes the Singular Value Decomposition; U and D are incrementally updated eigenvectors and eigenvalues. An exemplary algorithm to incrementally estimate multiple sparse eigenvectors from a time-varying similarity matrix is shown in Algorithm 1 below:

---

Algorithm 1

---

Input: similarity matrix $\Sigma \in \mathbb{R}^{n \times n}$, eigenvectors U, eigenvalues D
1: $\rho = 0.25$ (sparsity), N = 100 (iteration times)
2: for k = 1, 2, ..., N do
3: $\quad \beta_k = \frac{1}{n} Tr(\Sigma \Sigma_k) + \frac{\rho}{n} \|\Sigma_k\|_1$
4: $\quad Z_k = \Sigma - \frac{\sqrt{k}\rho}{2\sqrt{2}} \Sigma_k + \frac{\sqrt{k}\rho}{2\sqrt{2}} sign(\Sigma_k) \odot \left( |\Sigma_k| - \frac{2\sqrt{2}}{n\sqrt{k}} \right)$
5: $\quad X = \{x_1, x_2, \ldots, x_m\} \leftarrow$ multiple eigenvectors of $Z_k$, where m is determined by Eq. 15 and Eq. 16
6: $\quad \hat{\Sigma} = X X^T$
7: $\quad \Sigma_{k+1} = \left(1 - \frac{2}{k+1}\right) \Sigma_k + \frac{2}{k+1} \hat{\Sigma}$
8: $\quad$ if $\frac{|\beta_k - \beta_{k-1}|}{\beta_k} < 10^{-3}$ then
9: $\quad\quad$ break
10: $\quad$ end if
11: end for
12: if U, D == 0 then
13: $\quad$ [U, D, V] = SVD($\hat{\Sigma}$)
14: else
15: $\quad$ [U, $\hat{\Sigma}'$]R = QR([U D, $\hat{\Sigma}$]) $\leftarrow$ solved by QR decomposition
16: $\quad$ [U', D', V'] = SVD(R)
17: $\quad$ $U_m' \in U', D_m' \in D' \leftarrow$ select top m eigenvectors and eigenvalues, where m is determined by Eq. 16
18: $\quad$ U = sign(U) $\odot$ |[U', $\Sigma_{new}'$]$U_m'$|, D = $D_m' \leftarrow$ update subspace model
19: end if
Output: updated U and D

---

Hierarchical Fusion—

Figure 9:
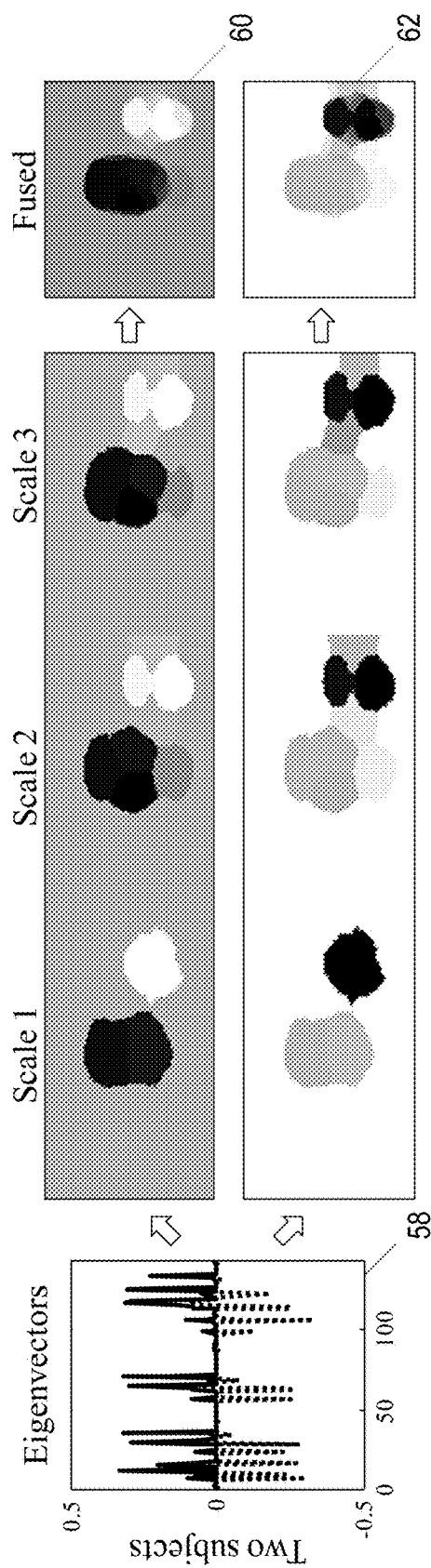
FIG. 9 illustrates the projection of eigenvectors onto hierarchical voxels and a fused map indicating which parts of the video sequence correspond to living skin tissue.

By projecting the estimated sparse eigenvectors 56, 58 onto the hierarchical voxels, a voxel-based human objectness map in multiple scales is obtained, where each scale has a different quantized description to the subject. This projection for the video sequence containing two subjects from FIGS. 7 and 8 is illustrated in FIG. 9. The eigenvector 58 not only decides the subject direction (sign) in subspaces, but also decides the pulsatility (amplitude) of corresponding skin-regions, i.e., forehead and cheek show relatively high pulsatility in projection. The final step is to fuse multiple objectness maps into a single output. Due to the fact that hierarchical measurement creates a statistical observation for skin-regions, the basic idea is to exploit this redundancy to derive a single output for which all scales have the highest agreement. In this sense, the hierarchical fusion is cast as the energy minimization between multiscale objectness maps as:

$$\operatorname*{argmin}_{\hat{O}}(\gamma E_1 + (1-\gamma)E_2), \quad (18)$$

with $$\begin{cases} E_1 = \sum_i \sum_j \|o_{ij}, \hat{o}\|_2 \\ E_2 = \sum_i \left( \sum_{\substack{j \\ o_{ij} \subseteq o_{i-1,j}}} \|o_{ij}, o_{i-1,j}\|_2 + \sum_{\substack{j \\ o_{i+1,j} \subseteq o_{ij}}} \|o_{ij}, o_{i+1,j}\|_2 \right), \end{cases} \quad (19)$$

where $O_{ij}$ corresponds to the objectness value of j-th voxel in i-th scale that determined by the eigenvector elements; $\hat{O}$ denotes the fused objectness map; $\gamma$ controls the balance between two energy terms. In equation 19, $E_1$ minimizes the energy between inputs and output, while $E_2$ minimizes the energy between spatially overlapped voxels in different scales, i.e., an implicit tree structure. FIG. 9 shows an example of the fused result in the video sequence with two alive subjects, where separate outputs 60, 62 are provided for each of the identified subjects.

The above method, and the preferred embodiment of the VPS method, provide an improved method and apparatus for identifying living skin tissue in a video sequence. In particular the method provides improved living skin tissue detection rates compared to conventional techniques, with the detection being based solely on using pulse signals to detect living tissue. These improvements are obtained regardless of the scale (i.e. distance from the imaging unit 4), posture, position, skin tone, visible body part or motion of the subject, or background of the subject in the video sequence, whether the subject is partially occluded from the imaging unit 4, whether there is an artificial face or body part present in the video sequence, or whether there are multiple living subjects in the video sequence.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:
1. An apparatus for identifying living skin tissue in a video sequence, the apparatus comprising:
   a processor; and
   a computer readable medium having computer readable code that on execution by the processor operates to:
      receive a video sequence, the video sequence comprising a plurality of image frames;
      divide each of the image frames into a plurality of frame segments, wherein each frame segment is a group of neighboring pixels in the image frame, by grouping pixels into frame segments based on color and spatial similarities of the pixels;

form a plurality of video sub-sequences, each video sub-sequence comprising a frame segment from two or more of the plurality of image frames, by, for each video sub-sequence, selecting frame segments from each of the plurality of image frames such that a difference between the chrominance of the frame segments in the video sub-sequence is minimized by identifying frame segments in a next image frame relative to a current image frame that have a smallest difference in chrominance to corresponding frame segments in the current image frame;

analyze the plurality of video sub-sequences to determine a pulse signal for each video sub-sequence;

determine a similarity matrix based on pairwise similarities for each determined pulse signal with each of the other determined pulse signals; and identify areas of living skin tissue in the video sequence from the similarity matrix.

2. An apparatus as claimed in claim 1, wherein the pairwise similarity for a pulse signal and one of the other pulse signals comprises one or more of:

a correlation between at least part of the frequency spectra of the two pulse signals;

a normalized cross correlation between at least part of the frequency spectra of the two pulse signals;

a measure of the entropy of the correlation between at least part of the frequency spectra of the two pulse signals; and the result of an inner product of the two pulse signals.

3. An apparatus as claimed in claim 1, wherein the pairwise similarities include frequency-based pairwise similarities.

4. An apparatus as claimed in claim 1, wherein the processing unit is configured to identify areas of living skin tissue in the sequence of images from the similarity matrix by performing matrix decomposition on the similarity matrix.

5. An apparatus as claimed in claim 1, wherein the processing unit is configured to form a plurality of video sub-sequences by, for each video sub-sequence, by further selecting frame segments from each of the plurality of image frames such that a difference between a spatial-distance between the position of the frame segments in the video sub-sequence is minimized.

6. An apparatus as claimed in claim 1, the processing unit being further configured to:

determine one or more physiological characteristics from one or more pulse signals associated with the identified areas of living skin tissue in the video sequence.

7. An apparatus as claimed in claim 1, wherein the apparatus further comprises:

a camera for capturing the video sequence.

8. A method for identifying living skin tissue in a video sequence, the method comprising:

obtaining a video sequence, the video sequence comprising a plurality of image frames;

dividing each of the image frames into a plurality of frame segments by grouping pixels into frame segments based on color and spatial similarities of the pixels, wherein each frame segment is a group of neighboring pixels in the image frame;

forming a plurality of video sub-sequences, each video sub-sequence comprising a frame segment from two or more of the plurality of image frames, by for each video sub-sequence, selecting frame segments from each of the plurality of image frames such that a difference between the chrominance of the frame segments in the video sub-sequence is minimized;

analyzing the plurality of video sub-sequences to determine a pulse signal for each video sub-sequence;

determining a similarity matrix based on pairwise similarities for each determined pulse signal with each of the other determined pulse signals; and identifying areas of living skin tissue in the video sequence from the similarity matrix.

9. A method as claimed in claim 8, wherein the pairwise similarities include frequency-based pairwise similarities.

10. A method as claimed in claim 8, wherein identifying areas of living skin tissue in the sequence of images from the similarity matrix comprises performing matrix decomposition on the similarity matrix.

11. A method as claimed in claim 8, wherein analyzing the video sub-sequences to determine a pulse signal comprises:

averaging pixel values for each pixel in a frame segment; and forming the pulse signal for a video sub-sequence from the averaged pixel values for each frame segment in the video sub-sequence.

12. A method as claimed in claim 11, wherein averaging pixel values comprises:

weighting the pixel values of pixels in a frame segment, wherein the pixel values are weighted based on spatial position of the pixel in the frame segment and/or a difference in color with a pixel or group of pixels at or near the center of the frame segment; and averaging the weighted pixel values of pixels in a frame segment.

13. A non-transitory computer readable medium having computer readable code embodied therein, the computer readable code being configured such that, on execution by a suitable computer or processor, the computer or processor is caused to perform a method comprising:

obtaining a video sequence, the video sequence comprising a plurality of image frames;

dividing each of the image frames into a plurality of frame segments by grouping pixels into frame segments based on color and spatial similarities of the pixels, wherein each frame segment is a group of neighboring pixels in the image frame;

forming a plurality of video sub-sequences, each video sub-sequence comprising a frame segment from two or more of the plurality of image frames by, for each video sub-sequence, selecting frame segments from each of the plurality of image frames such that a difference between the chrominance in the chromatic plane of the frame segments in the video sub-sequence is minimized;

analyzing the plurality of video sub-sequences to determine a pulse signal for each video sub-sequence;

determining a similarity matrix based on pairwise similarities for each determined pulse signal with each of the other determined pulse signals; and identifying areas of living skin tissue in the video sequence from the similarity matrix.

14. A non-transitory computer readable medium as claimed in claim 13, wherein the pairwise similarities include frequency-based pairwise similarities.

15. A non-transitory computer readable medium as claimed in claim 13, wherein identifying areas of living skin tissue in the sequence of images from the similarity matrix comprises performing matrix decomposition on the similarity matrix.

16. A non-transitory computer readable medium as claimed in claim 13, wherein analyzing the video sub-sequences to determine a pulse signal comprises:
   averaging pixel values for each pixel in a frame segment; and
   forming the pulse signal for a video sub-sequence from the averaged pixel values for each frame segment in the video sub-sequence.

17. A non-transitory computer readable medium as claimed in claim 16, wherein averaging pixel values comprises:
   weighting the pixel values of pixels in a frame segment, wherein the pixel values are weighted based on spatial position of the pixel in the frame segment and/or a difference in color with a pixel or group of pixels at or near the center of the frame segment; and
   averaging the weighted pixel values of pixels in a frame segment.

18. A non-transitory computer readable medium as claimed in claim 13, wherein the method further includes:
   determining one or more physiological characteristics from one or more pulse signals associated with the identified areas of living skin tissue in the video sequence.

* * * * *